(12) United States Patent
Hageman

(10) Patent No.: US 8,388,949 B2
(45) Date of Patent: Mar. 5, 2013

(54) COMPOSITIONS COMPRISING PANTOTHENIC ACID AND THEIR USE FOR STIMULATING APPETITE

(75) Inventor: Robert Johan Joseph Hageman, Wageningen (NL)

(73) Assignee: N.V. Nutricia, Zoetermeer (NL)

( * ) Notice: Subject to any disclaimer, the term of this patent is extended or adjusted under 35 U.S.C. 154(b) by 1267 days.

(21) Appl. No.: 10/584,510

(22) PCT Filed: Dec. 24, 2004

(86) PCT No.: PCT/NL2004/000910
§ 371 (c)(1),
(2), (4) Date: May 14, 2007

(87) PCT Pub. No.: WO2005/060952
PCT Pub. Date: Jul. 7, 2005

(65) Prior Publication Data
US 2008/0031860 A1 Feb. 7, 2008

(30) Foreign Application Priority Data
Dec. 24, 2003 (EP) .................................... 03079190

(51) Int. Cl.
*A61K 38/43* (2006.01)
(52) U.S. Cl. ........ 424/94.1; 514/727; 514/738; 514/739
(58) Field of Classification Search .................. None
See application file for complete search history.

(56) References Cited

U.S. PATENT DOCUMENTS

| 4,474,812 A | 10/1984 | Cavazza |
| 4,497,800 A * | 2/1985 | Larson et al. ..................... 514/2 |
| 6,036,984 A | 3/2000 | Sartorio et al. |
| 6,245,803 B1 | 6/2001 | Acosta et al. |
| 6,322,821 B1 | 11/2001 | Register |
| 6,544,515 B1 | 4/2003 | Dangin et al. |
| 6,846,494 B1 * | 1/2005 | Verheul-Koot et al. ........ 424/439 |
| 2002/0001575 A1 * | 1/2002 | Foreman ..................... 424/93.3 |
| 2009/0124551 A1 * | 5/2009 | Reid et al. ....................... 514/12 |

FOREIGN PATENT DOCUMENTS

| CA | 1228819 A | 11/1987 |
| DE | 4304394 | 9/1993 |
| DE | 29916231 | 9/1999 |
| EP | 0 611568 | * 8/1994 |
| GB | 2236675 A | 4/1991 |
| JP | 7233070 A | 9/1995 |
| JP | 2001008637 | 1/2001 |

OTHER PUBLICATIONS

Priya Chemicals "Amino Acid Composition: Protein Hydrolysate Soln. (Casein Base)." (No publicaton date) Accessed Jun. 16, 2010. URL: http://www.priyachem.com/casesoy.htm.*
Kirkman Group "Pea Protein Powder." (No publication date) Accessed Jun. 17, 2010. URL: http://www.kirkmanlabs.com/ViewProductDetails@Product_ID@56@Product_Group_ID@1. aspx.*
Virgin Coconut "Essential Facts: Fatty Acids Composition of Virgin Coconut Oil." (No publication date) Accessed Jun. 17, 2010, URL: http://www.thevirgincoconutoil.com/articleitem.php?articleid=163.*
Sindayikengera et al, J Zhejiang Univ Science B, 2006, vol. 7, No. 2, pp. 90-98.*

* cited by examiner

*Primary Examiner* — Allison Ford
(74) *Attorney, Agent, or Firm* — The Webb Law Firm

(57) ABSTRACT

The invention relates to the field of food compositions and their use. In particular compositions comprising at least 15 En % protein and pantothenic acid, or equivalents thereof, are provided, which are suitable for stimulating appetite.

25 Claims, No Drawings

COMPOSITIONS COMPRISING PANTOTHENIC ACID AND THEIR USE FOR STIMULATING APPETITE

FIELD OF THE INVENTION

The present invention relates to the field of food compositions and their use. In particular compositions comprising pantothenic acid, or equivalents thereof, are provided, which are suitable for stimulating appetite.

BACKGROUND OF THE INVENTION

Pantothenic acid is a water-soluble vitamin, also known as vitamin B5, which is a component of coenzyme A (CoA). Pantothenic acid is found in a large range of foods, such as fish, meat, eggs, milk products and vegetables, as a result of which natural deficiency is very rarely observed in humans. In the past studies have been carried out in which pantothenic acid deficiency has been induced experimentally in humans by administration of a pantothenic acid deficient diet (e.g. Fry et al. 1976, J. Nutr. Sci. Vitamology 22, 339-346) and/or a compound like omega-methyl pantothenic acid which is known to exhibit an anti-pantothenic acid-like effect (see e.g. Hodges et al. 1959, J. Clin. Invest. 38, 1421-1425). Symptoms exhibited by the participants of such trials were gastrointestinal complaints (nausea, vomiting, abdominal cramps), irritability, restlessness, fatigue, apathy, malaise, headache, insomnia, numbness or tingling of feet and hands, parasthesia, muscle cramps, staggering gait, hypoglycaemia and increased sensitivity to insulin (see e.g. Hodges et al. 1958, J. Clin. Invest. 37, 1642-1657; Report "Expert Group on Vitamins and Minerals 2003" published by the Food Standards Agency, Aviation House, 125 Kingsway, London WC2B 6NH, UK). In other studies, where humans were on a pantothenic acid free diet, no clinical signs of deficiency developed (Fry et al. 1976, J. Nutr. Sci. Vitminol. 22(4), 339-346. It is concluded that none of the above studies reveal that pantothenic acid deficiency is related to the loss of appetite or that pantothenic acid can be used to restore appetite loss. These studies neither reveal that pantothenic acid can be used to restore bodyweight. It is particularly noted that increased demands for pantothenic acid have never been associated with severe illnesses such as cancer, AIDS, catabolism as a result of respiratory diseases such as lung emphysema, severe traumata such as surgery and severe diarrhea such as for instance occurring with inflammatory bowel disease. In other words it is generally not believed that bad appetite and weight loss associated with any severe illness is caused by a pantothenic acid deficiency.

Vaughan and Vaughan (J. Nutrition, (1960) 70: 77-80) described the effect of cold on weight, food intake and acetylating acitivity of pantothenic acid deficient rats. They present some data from which it may derived that healthy rats, that are brought in a pantothenic acid-deficient state by feeding for 33 days an artificial diet that uses casein as protein source and vegetable oil as lipid source but which is devoid of pantothenic acid, benefit from the administration of pantothenic acid in terms of increase in weight and of food intake. The authors concluded however that there was no relation between level of pantothenic acid and food intake and that pantothenic acid does not have an influence on growth which is related to appetite. Moreover, no relation is made to a potential beneficial effect in human patients that have a completely different taste perception and especially no relation is made to human beings that suffer from terminal cancer, AIDS, COPD or other severe disorders.

EP 0914111 relates to methods and nutritional compositions for the prevention and treatment of cachexia and anorexia. In this document there is no suggestion of a beneficial effect of pantothenic acid to appetite, nor was indicated that the amount of saturated fatty acids, in particular myristic acid is of any relevance.

DE 4304394 concerns preparations for enteral feeding of oncologic patients to overcome problems related to weight loss. The preparations are characterised by a balanced composition of specific types of fats. Also preparations are disclosed that include calcium pantothenate and pantothenic acid but no relation between the level of pantothenic acid and stimulating appetite was mentioned or suggested.

Several documents such as DE 29916231, JP 5294833 and U.S. Pat. No. 6,322,821 describe multivitamin compositions including calcium pantothenate that are useful to treat amongst others loss of appetite in humans and cows. Neither of these documents however disclose a critical role for the level of pantothenic acid in the compositions.

No recommended dietary allowance (RDA) for pantothenic acid intake has been set by the Food and Nutrition Board of the Institute of Medicine (Eissenstat et al. 1986, Am. J. Clin. Nutr. 44(6), 931-937). Instead, only approximate adequate daily dietary intake values (AI) have been described for different age or target groups, ranging from 1.7 mg/day in infants to 4-5 mg/day in adults and 6-7 mg/day in pregnant or breastfeeding women (Department of Health, 1991, In: Dietary reference values for food, energy and nutrients for the United Kingdom. HMSO, London, p113-115). Also, no tolerable upper level for pantothenic acid has been set, as there seems to be no adverse effect of consumption of large amounts. The only reported adverse effect described is the occurrence of diarrhea, associated with intake of 10-20 mg calcium D-pantothenate per day (Flodin 1988, Pharmacology of micronutrients; New York, Alan R. Liss, Inc.). The UK Council for Responsible Nutrition has recommended an Upper Safe Level of pantothenic acid of 1000 mg/day for long and short term supplementation (leaflet CRN 1999, The safe use of supplements benefit good health).

Apart from dietary pantothenic acid uptake, bacteria colonising the colon are also able to produce pantothenic acid, and it is therefore feasible that the pantothenic acid produced in the subject's intestine is adsorbed and provides a further source of this vitamin (Said et al. 1998, Am. J. Physiol. 275:C1365-1371). However, it is not known whether internally produced pantothenate contributes in significant amounts to the body's overall pantothenate levels. In experimental set-ups, the internal bacterial production of pantothenic acid often necessitates treatment with antibiotics in order to elicit pantothenic acid deficiency in test animals (Stein and Diamond 1989, J. Nutr. 119(12), 1973-1983).

Commercially available vitamin supplements mostly also contain pantothenic acid, or derivatives thereof, such as calcium pantothenate, sodium pantothenate or panthenol, which are more stable than pantothenic acid. Mostly the D-isomer is used, although DL-raceniic mixtures may also be used. Pantothenate, which is taken up with the diet, is adsorbed in the intestine and transported via the blood (primarily as bound forms within erythrocytes) to various body tissues. The majority of tissues import pantothenic acid from the blood via an active sodium-dependent co-transport mechanism. Blood plasma levels of pantothenic acid have not been found to correlate well with dietary intake levels, while a good correlation between urinary excretion of pantothenate and dietary intake has been found (Eissenstat et al. 1986, American J. of Clinical Nutrition 44, 931-937).

Dietary pantothenic acid supplements have been proposed to have a beneficial effect in the treatment of obesity. Leung 1995, Medical Hypotheses 44, 403-405) describes that, when the intake of a low calorie containing diet (about 1000 calories/day) is supplemented by co-administration of large daily amounts of pantothenic acid (about 10 g/day), a gradual weight loss of about 1 kg per week is achieved while dieters do not feel hunger or weakness and ketone body formation is significantly reduced (only detectable in trace amounts in the urine). In particular, it is suggested that pantothenic acid may be called a 'hunger suppressant' when taken at a large dose during periods of low calorie intake.

This disclosure does, however, not suggest any other uses for pantothenic acid than the supplementation of low calorie diets in order to solve the problem of hunger, weakness and ketone body formation associated with dieting. Further, it clearly teaches the use of pantothenic acid as a hunger suppressant. In contrast hereto, the present inventors found that the administration of compositions comprising pantothenic acid, or equivalents thereof, to subjects suffering from lost appetite, especially lack of appetite resulting from diseases or disease therapies, stimulates appetite or hunger and increases body weight and muscle mass in (specific groups of) humans.

Myristic acid is a saturated fatty acid, like for example lauric acid, palmitic acid and stearic acid which occurs in a few vegetable oils like coconut oil. In small quantities it therefore may be present in artificial clinical nutrition. Saturated fatty acids are considered as an undesirable lipid component which may cause cardiovascular problems. Saturated fatty acids and coconut oil are difficult to use in the manufacture of liquid formulas because they can cause excessive creaming and therefore inclusion thereof is avoided in the state of the art. Instead corn oil, rapeseed oil, sunflower or soybean oil are included which form homogeneous emulsions in complete formulae and comprise <0.5% myristic acid. These also comprise high amounts of linoleic acid which is considered highly desirable.

DETAILED DESCRIPTION OF THE INVENTION

Definitions

"Pantothenic acid" or "pantothenate" or "vitamin B5" refers to a pantoic acid moiety amide linked to a beta-alanine subunit (pantoyl beta-alanine). This definition is limited to the active stereoisomer of pantothenate, namely the D-isomers of pantothenate.

"Pantothenic acid derivatives" or "pantothenic acid equivalents" is used herein to refer to compounds derived from pantothenic acid and which have an equivalent or improved appetite stimulating effect as that of pantothenic acid, such as but not limited to: salts (e.g. calcium pantothenate, sodium pantothenate), esters or ethers of pantothenic acid; pantothenol (or panthenol, pantothenyl alcohol); (R)-pantoate or its salts, esters or ethers; pantetheine (pantothenic acid linked to a beta-mercaptoethylamine group) or its salts, esters or ethers, like S-acetyl pantetheine; Coenzyme A (CoA), which is composed of 4'-phosphopantetheine linked by an anhydride bond to adenosine 5'-monophosphate, modified by 3'-hydroxyl phosphate; including e.g. acetyl CoA, succinyl CoA, etc. Again, in particular the active D-isomers are referred to, such as for example D-calcium pantothenate.

"Loss of appetite" or "appetite loss" refers to a loss of desire to consume food, in particular for more than a few days, such as 1-5 days.

"Enteral" refers herein to the delivery directly into the gastrointestinal tract of a subject (e.g. orally or via a tube, catheter or stoma).

"Parenteral" refers herein to the delivery other than to the gastrointestinal tract, in particular, intravenously to the blood, subcutaneously, intramuscularly, and the like.

"Administration" is used herein to refer to enteral or parenteral delivery to a subject, by someone else or by the subject himself. It is, therefore, understood that for example food consumption by the subject is also referred to.

"Food" is used herein to refer to include liquids, such as beverages.

"Food composition" refers herein to a composition suitable for administration to a human subject, comprising at least 15 En % (energy percent) proteins (or hydrolysed proteins or amino acids) and/or at least 32 En % carbohydrates and/or at least 18 En % lipids and provides at least 100 kcal per daily dose. In one embodiment, the composition comprises at least 15 En % proteins (or hydrolysed proteins or amino acids) and at least 25 En % lipids and at least 40 En % carbohydrates. In order to contribute better to the complete nutrition of humans also one or more vitamins, minerals, trace elements and other food components can be included such as dietary fiber, creatine and/or carnitine. Complete food composition should comprise all these.

The term "comprising" is to be interpreted as specifying the presence of the stated parts, steps or components, but does not exclude the presence of one or more additional parts, steps or components.

Loss of appetite is a serious symptom, which often leads to undesired weight loss and enhances the catabolic processes that often occur due to diseases, illnesses or disorders, or as a side effect of disease treatment or therapy or following surgery. Appetite loss has been described by cancer patients, HIV infected patients or patients with AIDS, subjects suffering from severe respiratory diseases, catabolic diseases, subjects suffering from serious diarrhea (such as the diarrhea that is associated with inflammatory bowel diseases or Crohn's Disease) or from traumata following surgery, subjects undergoing or having undergone chemo- or radiotherapy treatment, and the like.

Good nutrition is necessary to help overcoming the disease or disorder itself or its treatment effects and to rebuild body strength. If persisting over longer periods, appetite loss can lead to serious weight loss and anorexia, and will slow down or prevent recovery of the patient, and may even lead to the patient's death. In cancer treatment, for example, the importance of nutrition in determining cancer survival is well recognized, as there is an exponential increase in mortality when body mass index falls below 20. In addition, lack of appetite and ensuing weight loss often causes psychological distress to both patients and relatives.

Currently, different ways to stimulate appetite are being used, depending on the associated condition or treatment. In addition to special diets and care of dieticians (e.g. trying to motivate the patient to eat by reducing meal sizes, increasing meal frequency, varying flavour, and the like), appetite stimulating compositions (i.e. appetite stimulants) are frequently administered. For example, orexigenic agents (e.g. progesterones, corticosteroids and cannabinoids) help to stimulate appetite and are often used to treat anorexia/weight loss.

Chemotherapy patients relatively frequently receive dronabinol (a synthetic cannabinoid), which has a dual role, in that it reduces chemotherapy-induced nausea and vomiting and also stimulates appetite. Dronabinol is administered orally in capsule form and is manufactured in measured doses of either 2.5 mg, 5 mg or 10 mg capsules, allowing for flexible and individualized dosing. Dronabinol is also used in other situations for the treatment of weight loss and anorexia. It is reported that after just 4 weeks of therapy, dronabinol significantly stimulates appetite and elicits trends toward improved body weight and mood and decreased nausea in immunodeficiency syndrome patients with anorexia associated with weight loss.

Although a number of appetite stimulants exist, there is a general need for new appetite stimulants, preferably stimulants, which do not have undesired side effects. As the existing appetite stimulants comprise pharmaceutical drugs, which require extensive and costly governmental approval procedures, it would be beneficial to provide food or food supplement compositions, which are based on natural substances that are recognised as harmless, even when consumed in large quantities. Also, the presently used appetite stimulants do not replace the need of patients to consume food, or take in nutrients in some way, as the appetite stimulants are not food compositions as such, but generally only supplement food intake.

In one embodiment the invention provides a food composition (as defined above) comprising pantothenic acid or one or more equivalents thereof. Preferably, the food composition comprises at least 14 mg pantothenic acid, or of at least one equivalent thereof, per daily dosage. It is preferred that the food composition further comprises at least 4 wt % protein (or hydrolysed protein or amino acids) per daily dosage and/or at least 1.5 wt % of a lipids. The weight percentage is the weight amount of a component per 100 g of composition.

In another embodiment of the invention the food composition is a complete food composition, which refers to a composition, which provides proteins (or hydrolysed proteins or amino acids) and/or lipids and/or carbohydrates in a sufficient amount to provide the daily calorie intake required for normal body health. This means that a subject does not need to (although he/she may) consume or be administered any other food while consuming or being administered the complete food composition (meal replacement). The complete food composition preferably comprises at least 14 mg pantothenic acid, or an equivalent thereof, per daily dosage. As the desire is that the treated subject does not lose weight, but preferably gains weight, it is preferred that the complete food composition is high in calories. Preferably, it comprises at least 600 kcal, more preferably at least 900 kcal, or at least 1200 kcal or more per daily dose.

The food composition and the complete food composition according to the invention comprise a sufficient amount of pantothenic acid, or of at least one equivalent thereof, to stimulate appetite (or to prevent appetite loss) in humans, when taken by or administered to a subject suffering from appetite loss (or at high risk of developing appetite loss) over a sufficient period of time, preferably a couple of days, for example at least 2 days, to at least a couple of weeks, for example at least 2 weeks (herein referred to as an "effective dose"). A skilled person can easily determine using known methods, whether a composition as described herein has the desired appetite stimulating effect. For example, patients suffering from appetite loss are randomly divided into two groups. The composition comprising pantothenic acid, or at least one equivalent thereof, is administered to one group over several weeks, while the other groups is administered an equivalent composition lacking pantothenic acid (or an equivalent thereof). Appetite is recorded over several weeks and the two groups are compared. Preferably also weight is recorded. Standard statistical methods can then be used to determine whether the composition has a significant appetite stimulating effect.

It is also an object of the invention that both the food composition and the complete food composition lead to stable body weight, more preferably to weight increase of the subject when administered in an effective dose over a period of several weeks or months. This can be easily determined by weighing subjects at regular intervals, at least once a week, preferably daily. It is not a requirement that the increase in body weight is solely due to administration of the composition. Clearly, as appetite is stimulated, it may be an effect of the subject consuming more food voluntarily. However, administration of a complete food composition preferably in itself provides sufficient nutrients and daily calorie intake to stabilize and/or increase body weight.

The food composition or complete food composition preferably comprises at least 14 mg of pantothenic acid, or an equivalent thereof, per daily dose. More preferably, the composition comprises at least 15 mg, even more preferably at least 18 mg, or even better 25-1000 mg (such as 25, 26, 27, 28, . . . , 1000 mg per daily dose. When a pantothenic acid equivalent is used, particularly pantothenol, (R)-pantoate or salts or esters thereof, or pantetheine or salts or esters thereof, the composition preferably comprises at least an equimolar amount of 14 mg pantothenic acid per daily dose.

The protein component of the food or complete food composition may be composed of complete proteins, hydrolysed proteins, partially hydrolysed proteins or amino acids, or mixtures of any of these. The protein component of the composition is preferably at least 4 wt %, 5 wt %, 10 wt % or more per daily dose. In one embodiment at least 20%, more preferably at least 30% or 50% or more of the total protein is whey protein, preferably acidic whey. As mentioned, the protein component may be hydrolysed, although the use of intact or only partially hydrolysed (small peptides) is preferred.

In a further embodiment the protein component of the composition consists of plant proteins, such as for example (partially) hydrolysed plant proteins, for example proteins extracted from protein storage tissue such as tubers and seeds, for example protein from potato tubers, cereal protein e.g. from wheat, buck-wheat, barley, rye, oat, corn, rice, from beans (for example soybean, kidney bean, white bean, etc.), protein from peas, protein from seeds, such as sunflower seeds, cashew nuts, peanuts, oilseed rape seeds, lupine seeds, etc. In principle any plant protein composition may be used, which is safe to humans and can be obtained food grade. Preferably the protein composition used is also not allergenic to humans. If potentially allergenic components are present, these may be removed prior to use.

The protein component used preferably comprises sufficient amounts of methionine and lysine. The proportion of methionine is preferably 1.8-6 wt % of total amino acids (such as 2.0-5.0 wt %, or 2.3-4.0 wt %). Lysine is preferably present in the protein(s) in an amount of 5.8-12.0 wt % of total amino acids (such as 6.0-11.0 wt % or 6.5-10.0 wt %). Tryptophan is preferably present in the protein component in an amount of 1.5-4wt % (and more preferably in the concentration range 1.6-3.0 wt %) of total amlino acids. Leucine is preferably included in an amount of 8.0 wt % of the total amino acids and more preferably 8.5-35 wt % e.g in the range of 9-15 wt %.

In addition, the amino acid composition of the protein component used preferably has a high serine/glycine ratio. The serine/glycine ratio in the final composition is preferably 3.4 or higher.

Protein extraction from plant tissues, such as tubers or seeds, or the hydolysis thereof, can be done using methods known in the art. Instead of extracting proteins from natural sources, synthetic amino acids may also be used. Also short peptides with a desired amino acid composition may be synthesized chemically de novo, using for example an oligonucleotide synthesizer as supplied e.g. by Applied Biosystems Inc. (Fosters, Calif. USA). It is likewise possible to produce proteins or peptides with a desired amino acid composition by recombinant DNA methods, i.e. by expression in bacterial hosts, plants or plant cell cultures, animal cells, and the like, using methods known in the art.

The food composition or complete food composition preferably comprises sufficient amounts of the nine so-called "essential" amino acids (histidine, isoleucine, leucine, lysine, methionine and/or cysteine, phenylalanine and/or tyrosine, threonine, valine and tryptophan). For compositions administered to children arginine is preferably also present in sufficient amounts, i.e. in more than 3.8 wt. % preferably from 4.2 wt. %-7.2wt. % based on protein.

Clearly, any mixtures of the above described proteins and/or amino acids may be used to make the desired protein component for use in the food or complete food composition. For example, plant protein extracts and synthetic amino acids may be mixed in desired quantities to make a product with the desired amino acid constituents and proportions and the desired protein/peptide length (molecular weight distribution).

In one embodiment, the food or complete food composition preferably comprises at least one of the following components:

Cysteine or cysteine equivalents, preferably at least 0.2 g per daily dose, more preferably about 0.2-5 g per daily dose. Cysteine equivalents may for example be selected from one or more of 0.2-5 g L-cysteine, cysteamine, L-cystine or L-cystine dimer; 0.25-0.6 g N-acetyl cysteine; 0.2-5 g L-methionine (or any combination of these).

One or more nucleotides or nucleotide equivalents, preferably at least 0.2 g per daily dose, more preferably about 0.2-5 g per daily dose. Nucleotide equivalents may for example be selected from one or more of 1-10 g yeast, cytidine, uridine and/or nucleosides and ribose.

Beta-alanine, preferably at least about 0.1 g per daily dose, more preferably about 0.1-5 g per daily dose. Beta-alanine is preferably used in compositions comprising (R)-pantoate.

Folic acid or folic acid equivalents, preferably at least about 300 mg per daily dose, more preferably about 300-3000 mg per daily dose. Folic acid equivalents may for example be selected from one or more of mono- or poly-glutamate (reduced and/or oxidised forms), one carbon variants such as 5-methyl-, 10-methyl-, 5,10-methylene-, 5-formyl- or 10-formyl-folate.

Vitamin B6 or equivalents thereof, preferably at least about 0.5 mg per daily dose, more preferably at least about 0.5 to 50 mg per daily dose. Vitamin B6 equivalents may for example be selected from one or more of pyridoxine, pyridoxal or pyridoxamine.

Vitamins are preferably included in order to obtain maximum weight gain, in particular the vitamins folic acid, biotin, vitamin B2 and vitamin B6.

Preferably the amount of lipoic acid is lees than 50 mg/L, more preferably less than 33 mg/L in order to avoid aberrations in taste.

In a further embodiment lipids or a lipid fraction is included in the food or complete food composition in an amount of 1.5 g per 100 g composition. More preferably the amount of lipids is in the range of 2.0-10 g per 100 g composition, and most preferred it is 2.7-8 g per 100 g composition. The lipid fraction can be triglycerides, diglycerides, sterols, sphingolipids, ceramides, phospholipids, fatty acids and fatty acid esters. Preferably the lipid fraction has a relatively high amount of saturated fatty acids and in particular myristic acid for obtaining best results. The amount of saturated fatty acids preferably is more than 12 g per 100 g fatty acids and more preferably 14-50 g per 100 g fatty acids. The amount of myristic acid preferably is more than 4.0 g per 100 g fatty acids. Preferably the amount of myristic acid as % of the total amount of fatty acids is in the range 6-40 wt %, and most preferred is a concentration of about 8-30 wt % like 10-20 wt %. Additionally palmitic acid may be present in an amount of more than 9 wt % and preferably 10-35 wt %, like 12-25 g per 100 g fatty acids.

Myristic acid is preferably present as triglyceride, phospholipid, free fatty acid and/or an ester thereof. Suitable sources have a melting point below 55 and preferably below 50 degrees Celsius. This is achieved by fractioning lipids and selecting the ingredient, e.g. the triglyceride that complies with this criterion. These triglycerides will normally have fewer than 12 wt % and preferably less than 8 wt % stearic acid as based on the amount of fatty acids in the lipid source. These lipids comprise relatively high amounts of medium chain fatty acids, alpha-linolenic acid and oleic acid. The latter is generally above 15 wt %, while the amount of alpha-linolenic acid exceeds 12 wt %. The amount of linoleic acid will normally be below 45, preferably be below 38 and even more preferably below 30 g/100 g fatty acids.

Suitable sources of myristic acid are the free fatty acid, and esters like the propionyl or butyryl ester or the cetyl ester.

The relatively high amounts of saturated fatty acids in the lipid mixture makes that the amounts of unsaturated fatty acids, such as those of the (n-3), (n-6) and (n-9) series are relatively low. In particular the amount of (n-3) polyunsaturated fatty acids is below 30% calculated per 100 g fatty acids, and more preferred below 25% or even better below 20%. In particular the amounts of eicosapentaenoic acid and docosahexaenoic acid are relatively low, e. g 1-16 g/100 g fatty acids in order to prevent taste deterioration. It is well known that these fatty acids are extremely easy oxidized. It is therefore preferred to include an amount of (n-3) long chain fatty acids which is lower than the amount of (n-6) long chain fatty acids. When (n-3) long chain fatty acids are included in the product it is preferred to include them for more than 20% as alpha linolenic acid.

Phospholipids for example those that origin from soy, eggs or mammals milks can be included in an amount of 2-50 wt % of the lipid fraction, preferably 4-40% and most preferably 5-35 wt %. Especially phospholipids may be used that are rich in phosphatidylcholine, e.g. those that comprise more than 30% phosphatidylcholine and more preferably more than 35 wt % of the lipid fraction.

Other suitable choline sources are choline, betaine, dimethylglycine or sarcosine. In particular dimethylglycine or a betaine source can be applied in particular betaine base, salts thereof, e.g those with organic acids like citrate, pyruvate or malate in an amount of at least 0.5 g per daily dosis.

Cholesterol can be included in the lipid fraction in an amount of more than 1 wt %. Preferably the amount is about 2-10 g per 100 g lipids and most preferred is an amount of 2.5-6 wt %. Cholesterol can be included in many forms, e.g. as pure synthetic compound or as one or more types of cholesteryl-esters.

Minerals can be included as occurs in the state in the art of the manufacture of clinical nutrition. The amount of sodium should however be higher than normally used. Sodium levels preferably amount to 110-400 mg/100 ml liquid composition and more preferably 140-360 mg/100 ml composition.

A source of digestible carbohydrates is preferably also included in an amount of 32-60 en %. Suitable sources are known to those skilled in the art.

The method of administration of the compositions depends on the dosage form of the compositions. The composition is preferably in any liquid dosage form, such as a drink, an elixir, syrup, aerosols or a suspension. Alternatively it may be in solid dosage form (such as capsules, powders or tablets) or in semi-solid dosage forms (such as gels, creams).

Administration may be enteral (e.g. oral, by drinking/swallowing, tube feeding, etc.) or parenteral (e.g. intravenous injection). It is understood that the amount per daily dose can be subdivided into smaller effective amounts, which are then administered at different times during the day. Thus, when referring to a 'dosage per day' or 'daily dose', this does not imply that the dosage must be administered at one time. The compositions according to the invention may comprise additional active ingredients, such as other vitamins (A, B1, B2, B3, B12, C, D, E, K, etc.), folic acid, probiotics, prebiotics, and the like. The composition may also comprise other inactive ingredients and carriers, such as e.g. glucose, lactose, sucrose, mannitol, starch, cellulose or cellulose derivatives, magnesium stearate, stearic acid, sodium saccharin, talcum, magnesium carbonate and the like. The compositions may also comprise water, electrolytes, non-essential amino acids, trace elements, minerals, fiber, sweeteners, flavorings, colorants, stabilizers, preservatives, binders, fragrances, and the like.

When the composition is a drink, preferably the volume (comprising the daily effective dose) consumed or administered on a daily basis is in the range of 100-3000 ml per day. Especially during the first week(s) of administration, a small volume per day, such as 100 ml, 150 ml or 200 ml may be desired.

The food or complete food composition may also in one embodiment be made on the basis of (i.e. starting from or comprising) a food base. In one embodiment the food or complete food composition is based on, or comprises, a dairy product, such as a fermented dairy product, including but not limited to milk, yogurt, a yogurt-based drink or buttermilk. Such compositions may be prepared in a manner known per se, e.g. by adding an effective amount of pantothenic acid, or at least one equivalent thereof, to a suitable food or food base. Other food bases suitable may be plant bases, meat bases and the like. All embodiments described for food and complete food compositions also apply to a composition made on the basis of a food base, for example that the final composition preferably comprises at least 14 mg pantothenic acid or an equivalent thereof per daily dose. Evidently, if the food base itself already contains one or more of the components of the composition (e.g. pantothenic acid, cysteine, etc.), less of this component needs to be added to arrive at the desired dose of the final composition.

The food or complete food compositions according to the invention may be used either as a treatment and/or prophylactically. This is to say that they may be either administered after appetite loss has already been diagnosed in a subject or, alternatively, prior to the occurrence of symptoms of appetite loss.

In general any subject experiencing or likely to develop loss of appetite for more than a few days will benefit from the administration of the compositions according to the invention. Loss of appetite can have many causes: infections (such as pneumonia, hepatitis, HIV, influenza, pyelonephritis); serious liver, kidney or heart disease, such as chronic renal failure, congestive heart failure, cirrhosis; cancer of any kind, such as but not limited to colon-, stomach-, breast cancer, leukemia, etc.; intestinal obstruction; inflammatory bowel diseases, e.g. pancreatitis, irritable bowel syndrome, appendicitis; endocrine problems, e.g. diabetes or hypothyroidism; autoimmune diseases or disorders, such as rheumatoid arthritis, scleroderma; psychological conditions such as depression or schizophrenia; eating disorders, such as anorexia or bulimia; medications or drugs, in particular chemotherapy medications, alcohol, narcotis or antibiotics, diabetes medication (e.g. metformin); pregnancy; dementia (e.g. Alzheimer's); lung diseases, such as lung emphysema; traumata following surgery, and others.

In humans loss of appetite is easily recognized in subjects, by refusal to eat normal daily amounts, an aversion to food and/or drink. A composition according to the invention may be administered following the diagnosis of appetite loss or prophylactically, i.e. to subjects at high risk of developing loss of. For example the compositions may be given to subjects recently diagnosed of a certain disease or illness, or prior to starting a certain treatment (e.g. prior to chemotherapy), etc. The use a complete food compositions preferably substantially replaces normal nutrient intake, while the use of a food composition is preferably administered in addition to other nutrients.

When administering a composition according to the invention over several weeks, e.g. at least for 2 weeks, preferably at least 2-3 weeks, more preferably at least 2-4 or 2-6 weeks or more, the body weight of the subject preferably remains approximately constant (stable), more preferably increases during the administration period.

As a further beneficial effect of administration of a composition according to the invention, an increased chance of survival of subjects may be observed, a reduction of the toxicity of the medication in subjects may be observed, an increase of the sensitivity of insulin and a reduction or elimination of the occurrence of metastasis in cancer patients may be observed.

It is a further embodiment of the invention to provide a method for the manufacture of a composition according to the invention, i.e. a composition suitable for treatment or prophylaxis of appetite loss. The method comprises combining various ingredients in suitable amounts. A suitable amount of pantothenic acid or an equivalent thereof is in a daily dosage of at least 14 mg and suitably this dosage is administered to humans. In particular, a suitable amount of pantothenic acid, or at least one equivalent thereof, is combined with one or more other components (such as for example other nutrients, amino acids, etc. as described above). In order to provide sufficient nutrients at least the presence of proteins (or hydrolysed proteins or amino acids) is beneficial. Proteins (or hydrolysed proteins or amino acids) should be present in at least 15 En %. Thus, the use of pantothenic acid, or at least one of its equivalents, for the manufacture of a composition for use in a method for stimulating appetite is one embodiment of the invention. The use of proteins (or hydrolysed proteins or amino acids) and pantothenic acid or an equivalent thereof for the manufacture of a composition that comprises at least 15 En % proteins (or hydrolysed proteins or amino acids) and that comprises in a daily dosage at least 14 mg pantothenic acid or an equivalent thereof for use in a method for stimulating appetite is another embodiment of the invention. In a further embodiment the use of pantothenic acid, or at least one of its equivalents, for the manufacture of a composition for use in a method for stabilisation and/or increase of body weight is provided. In a further embodiment the use of pantothenic acid, or at least one of its equivalents, for the manufacture of a composition for use in a method for treatment and/or prevention of appetite loss that often occur in (early) stages of pregnancy is provided. In yet a further embodiment the use of pantothenic acid, or at least one of its equivalents, for the manufacture of a composition for use in a method to treat nausea during pregnancy is provided. Preferably these methods comprise administration of a composition comprising a daily dose of pantothenic acid or an equivalent thereof of 14-1000 mg.

The components to be combined in the compositions described herein are all readily available to a skilled person. They can thus either be obtained or manufactured by a person skilled in the art. It is also within the remit of a skilled person to purify, extract, mix, stabilize and combine constituents of the components as required using known methods.

Pantothenic acid is commercially available, but can also be manufactured synthetically as described in WO03/29476, WO03/13452 and WO03/04673, incorporated herein by reference. Chemical synthesis of pantothenic acid involves the condensation of D-pantolactone with beta-alanine. The compound is freely soluble in water, stable in neutral solutions, but unstable in acids, bases and heat.

Alternatively pantothenic acid can be purified from natural sources, such as for example from microorganisms (e.g. bacteria), which synthesize pantothenic acid via an amide linkage of pantoic acid and beta-alanine subunits.

Equivalents of pantothenic acid can also be obtained or manufactured as known in the art. For example, commercially available calcium pantothenate is prepared synthetically from isobutyraldehyde and formaldehyde via 1,1-dimethyl-2-hydroxy-propionaldehyde and pantolactone.

The following non-limiting Examples describe compositions according to the invention. Unless stated otherwise, the practice of the invention will employ standard conventional methods of food technology, molecular biology, virology, microbiology or chemistry.

EXAMPLES

Example 1

Composition 1

Ready to drink oral supplement that comprises per 100 ml 100 kcal, 40 en % protein, 41.1 en % carbohydrate, 18.9 en % lipid.
- protein 10.0 g of which 4 g pea protein hydrolysate, 4 g potato protein hydrolysate, 1.2 g soy protein isolate, 0.2 g methionine, 0.2 g L-lysine and 0.2 g L-leucine, 0.1 g tryptophan, 0.05 g L-serine and 0.05 g N-acetyl cysteine.
- lipids 2.1 g based on milk fat, myristic acid, linseed oil and olive oil, which comprises 15 wt % myristic acid and 15 wt % palmitic acid,
- carbohydrates based on maltodextrines 10.3 g
- pantothenic acid 6 mg
- folic acid 150 µg
- vitamin B6 0.6 mg
- biotin 20 ug
- sodium 150 mg Other micronutrients follow general recommendations for clinical nutrition as known in the art.

It is prescribed a patient should consume at least 250 ml of this ready to drink supplement.

Example 2

Composition 2

Liquid composition that comprises per 100 ml 166 kcal of energy: protein contributes 18 en %, digestible carbohydrates 38.5 en % and lipids 43.4 en %.
- protein is 7.3 g acid whey fortified with 0.2 g L-methionine
- lipids is 8.0 g blend of coconut oil, olive oil, cetyl-myristoleate, soybean oil comprising 17 wt % myristic acid
- carbohydrates is 16 g of a blend of maltodextrines and glucose syrup A vitamin premix is added that provides vitamin A 164 µg RE, 1.4 µg vitamin D, 2.5 mg alpha TE, 11 µg vitamin K, 0.3 mg thiamine, 0.32 mg riboflavin, 3.6 mg NE niacin, 5 mg pantothenic acid, 0.6 mg vitamin B6, 100 mg folic acid, 0.6 ug vitamin B12, 8 ug biotin, 20 mg vitamin C.

A mineral, trace element premix is used which provides 200 mg sodium, 200 mg potassium, 120 mg chloride, 80 mg calcium, 75 mg phosphorus, 45 mg magnesium, 3.2 mg iron, 2.4 mg zinc, 360 ug copper, 0.66 mg manganese, 0.2 mg fluoride, 20 ug molybdenum, 11.4 ug selenium, 13.4 ug chromium and 26.6 ug iodide.

Further 200 mg betaine was included.

It is prescribed the drink should be consumed in an amount of 600-800 ml per day.

Example 3

Composition 3

Powder intended to be reconstituted in water in an amount of 21.5 g per 100 ml.

Energy 100 kcal wherein protein contributes 16 en %, digestible carbohydrates 49 en % and fat 35 en %.
- protein is 4.0 g of a mixture of rice protein hydrolysate and pea protein hydrolysate, fortified with 0.1 g L-serine, 0.1 g Lysine, 0.05 g L-methionine and 0.05 g L tryptophan
- lipids are 3.9 g of a mixture of 30% egg phospholipids and a blend of oils and myristic acid; the amount of the latter is 18 g/100 g fatty acids,
- carbohydrates is 12.2 g of a mixture of maltodextrines and 1 g ribose.

The mineral and vitamin premixes provide 2 mg S-acetyl pantetheine, 35 µg folic acid, 0.35 mg pyridoxal, 150 mg sodium, apart from the other microingredients whose levels are known in the art.

Dimethylglycine is 0.2 g.

Fructo-oligosaccharides (blend of inuline and hydrolyzed inulin) is included in an amount of 1.0 g It is prescribed an amount of 1500-2000 ml reconstituted drink should be consumed per day.

Example 4

Also an animal experiment could be designed to determine the appetite stimulating effect of pantothenic acid. For example, Male Wistar rats (HsdCpb:WU, Harlan, The Netherlands) aged 3 months and weighing ±240 gram at arrival are used. Appetite loss is induced in the animals by e.g. the induction of cancer, stress, surgery or any other relevant treatment. The rats are kept at 20±1° C., with lights on from 23.00 h (ZT 0) until 11.00 h (ZT 12), and with water and food (RMH-B standard lab chow, Hope Farms Woerden, The Netherlands) ad libitum unless mentioned otherwise.

The rats receive a permanent silicone cannula (I.D. 0.6 mm, O.D. 1.2 mm) in the stomach under Isoflurane/Oxygen/Nitrogen oxide anesthesia according to the method described by Strubbe et al. Physiol Behav. 1986;36:489-493. This is done to allow frequent and stress-free intragastric administration of components at freely moving rats. A seven days period of recovery is allowed, until animals regain their preoperative weight.

After surgery, rats are housed individually in cages suitable for online monitoring of food and drink consumption (UgoBasile, Italy). The effects of a composition comprising pantothenic acid, or at least one equivalent thereof, on the food and water consumption are monitored in a singular (placebo-controlled cross over) experiment. Each singular experiment lasted 4 days (96 hours). Body weight is daily appointed.

On day 1, food is removed two hours before the lights are switched off (ZT 10.00). At ZT 11.30 randomly assigned rats receive the composition comprising pantothenic acid, or at least one equivalent thereof (dissolved in a total volume of 1 ml water) or an isovolumic amount of water alone through the gastric cannula. At ZT 12.00 food is returned, and food and drink intake is monitored at 1, 2, 3, 4, 5, 6, 12, 24 and 48 h after administration.

On day 3 the protocol of day 1 is repeated. The rats that receive the composition comprising pantothenic acid, or at least one equivalent thereof on day 1 now receive the vehicle and vice versa. Also at ZT 12.00 food is returned and food and water consumption is monitored at 1, 2, 3, 4, 5, 6, 12, 24 and 48 hours.

The invention claimed is:

1. A composition for stimulating appetite in a human comprising in a daily dosage form pantothenic acid or an equivalent of pantothenic acid selected from the group consisting of a salt, an ester or an ether of pantothenic acid, pantothenol, (R)-pantoate or a salt or an ester thereof, pantetheine or an ester or an ether thereof and coenzyme A, wherein the daily dosage form of pantothenic acid is 14 to 1000 mg of pantothenic acid, and wherein the daily dosage form of the equivalent of pantothenic acid is an equimolar amount of 14 to 1000 mg of pantothenic acid; and further comprising at least 15 En % proteins that comprise 1.8 to 6 g of methionine per 100 g of the proteins, 5.8 to 12.0 g of lysine per 100 g of the proteins, 1.5 to 4.0 g of tryptophan per 100 g of the proteins and at least 8 g of leucine per 100 g of the proteins, and at least 40 En % carbohydrates and at least 25 En % lipids; wherein said composition having a caloric value of at least 100 kcal per daily dosage form.

2. The composition according to claim 1, wherein the proteins are selected from the group consisting of plant proteins, vegetable proteins, cereal proteins, seed proteins and whey proteins.

3. The composition according to claim 1, wherein the proteins comprise serine and glycine in a serine/glycine ratio of 3.4 or higher.

4. The composition according to claim 1, further comprising per daily dosage form 0.2 to 5 g of cysteine or one or more cysteine equivalents selected from the group consisting of cysteamine, L-cystine, L-cystine dimmer and N-acetyl cysteine.

5. The composition according to claim 1, wherein the lipids comprise at least 12 g saturated fatty acids per 100 g lipids.

6. The composition according to claim 1, wherein the lipids comprise at least 4.0 g myristic acid per 100 g the lipids.

7. The composition according to claim 1, further comprising per daily dose at least one component selected from the group consisting of 0.2 to 5 g nucleotide or one or more nucleotide equivalents selected from the group consisting of cytidine, uridine and nucleosides; 300 to 3000 mg folic acid or one or more folic acid equivalents selected from the group consisting of monoglutamate, poly-glutamate 5-methyl-folate, 10-methyl-folate, 5,10-methylene-folate, 5 formyl-folate and 10-formyl-folate; 0.5 to 50 mg vitamin B6 or one or more vitamin B6 equivalents selected from the group consisting of pyridoxine, pyridoxal and pyridoxamine; and 0.5 g of at least one choline source selected from the group consisting of choline, betaine, dimethylglycine and sarcosine.

8. The composition according to claim 1, further comprising per daily dose 0.1 to 5 g beta-alanine when the composition comprises the pantothenic acid equivalent (R)-pantoate.

9. A composition for stimulating appetite in a human comprising in a daily dosage form pantothenic acid or an equivalent of pantothenic acid selected from the group consisting of a salt, an ester or an ether of pantothenic acid, pantothenol, (R)-pantoate or a salt or an ester thereof, pantetheine or an ester or an ether thereof and coenzyme A, wherein the daily dosage form of pantothenic acid is 14 to 1000 mg of pantothenic acid, and wherein the daily dosage form of the equivalent of pantothenic acid is an equimolar amount of 14 to 1000 mg of pantothenic acid; and further comprising at least 15 En % proteins that comprise 1.8 to 6 g of methionine per 100 g of the proteins, 5.8 to 12.0 g of lysine per 100 g of the proteins, 1.5 to 4.0 g of tryptophan per 100 g of the proteins and at least 8 g of leucine per 100 g of the proteins, and optionally at least 32 En % carbohydrates and/or at least 18 En % lipids; wherein said composition having a caloric value of at least 100 kcal per daily dosage form, wherein the composition comprises the lipids in an amount of at least 1.5 g per 100 g composition, and wherein the lipids comprise at least 4.0 g myristic acid per 100 g the lipids.

10. The composition according to claim 9, wherein the proteins are selected from the group consisting of plant proteins, vegetable proteins, cereal proteins, seed proteins and whey proteins.

11. The composition according to claim 9, wherein the proteins comprise serine and glycine in a serine/glycine ratio of 3.4 or higher.

12. The composition according to claim 9, further comprising per daily dosage form 0.2 to 5 g of cysteine or one or more cysteine equivalents selected from the group consisting of cysteamine, L-cystine, L-cystine dimmer and N-acetyl cysteine.

13. The composition according to claim 9 wherein the caloric value is at least 600 kcal per daily dosage form.

14. The composition according to claim 9, wherein the lipids comprise at least 12 g saturated fatty acids per 100 g lipids.

15. The composition according to claim 9, further comprising per daily dose at least one component selected from the group consisting of 0.2 to 5 g nucleotide or one or more nucleotide equivalents selected from the group consisting of cytidine, uridine and nucleosides; 300 to 3000 mg folic acid or one or more folic acid equivalents selected from the group consisting of monoglutamate, poly-glutamate 5-methyl-folate, 10-methyl-folate, 5,10-methylene-folate, 5 formyl-folate and 10-formyl-folate; 0.5 to 50 mg vitamin B6 or one or more vitamin B6 equivalents selected from the group consisting of pyridoxine, pyridoxal and pyridoxamine; and 0.5 g of at least one choline source selected from the group consisting of choline, betaine, dimethylglycine and sarcosine.

16. The composition according to claim 9, further comprising per daily dose 0.1 to 5 g beta-alanine when the composition comprises the pantothenic acid equivalent (R)-pantoate.

17. A composition for stimulating appetite in a human comprising in a daily dosage form pantothenic acid or an equivalent of pantothenic acid selected from the group consisting of a salt, an ester or an ether of pantothenic acid, pantothenol, (R)-pantoate or a salt or an ester thereof, pantetheine or an ester or an ether thereof and coenzyme A, wherein the daily dosage form of pantothenic acid is 14 to 1000 mg of pantothenic acid, and wherein the daily dosage form of the equivalent of pantothenic acid is an equimolar amount of 14 to 1000 mg of pantothenic acid; and further comprising at least 15 En % proteins that comprise 1.8 to 6 g of methionine per 100 g of the proteins, 5.8 to 12.0 g of lysine per 100 g of the proteins, 1.5 to 4.0 g of tryptophan per 100 g of the proteins and at least 8 g of leucine per 100 g of the proteins, and optionally at least 32 En % carbohydrates and/or at least 18 En % lipids; wherein said composition having a caloric value of at least 100 kcal per daily dosage form; further comprising per daily dose at least one component selected from the group consisting of 0.2 to 5 g nucleotide or one or more nucleotide equivalents selected from the group consisting of cytidine, uridine and nucleosides; 300 to 3000 mg folic acid or one or more folic acid equivalents selected from the group consisting of monoglutamate, poly-glutamate 5-methyl-folate, 10-methyl-folate, 5,10-methylene-folate, 5 formyl-folate and 10-formyl-folate; 0.5 to 50 mg vitamin B6 or one or more vitamin B6 equivalents selected from the group consisting of pyridoxine, pyridoxal and pyridoxamine; and 0.5 g of at least one choline source selected from the group consisting of choline, betaine, dimethylglycine and sarcosine.

18. The composition according to claim 17, wherein the proteins comprise serine and glycine in a serine/glycine ratio of 3.4 or higher.

19. The composition according to claim 17, further comprising per daily dosage faun 0.2 to 5 g of cysteine or one or more cysteine equivalents selected from the group consisting of cysteamine, L-cystine, L-cystine dimmer and N-acetyl cysteine.

20. The composition according to claim 17, wherein the caloric value is at least 600 kcal per daily dosage form.

21. The composition according to claim 17, wherein the lipids comprise at least 12 g saturated fatty acids per 100 g lipids.

22. The composition according to claim 17, wherein the lipids comprise at least 4.0 g myristic acid per 100 g the lipids.

23. The composition according to claim 17, further comprising per daily dose 0.1 to 5 g beta-alanine when the composition comprises the pantothenic acid equivalent (R)-pantoate.

24. A composition for stimulating appetite in a human comprising in a daily dosage form pantothenic acid or an equivalent of pantothenic acid selected from the group consisting of a salt, an ester or an ether of pantothenic acid, pantothenol, (R)-pantoate or a salt or an ester thereof, pantetheine or an ester or an ether thereof and coenzyme A, wherein the daily dosage form of pantothenic acid is 14 to 1000 mg of pantothenic acid, and wherein the daily dosage form of the equivalent of pantothenic acid is an equimolar amount of 14 to 1000 mg of pantothenic acid; and further comprising at least 15 En % proteins that comprise 1.8 to 6 g of methionine per 100 g of the proteins, 5.8 to 12.0 g of lysine per 100 g of the proteins, 1.5 to 4.0 g of tryptophan per 100 g of the proteins and at least 8 g of leucine per 100 g of the proteins, and optionally at least 32 En % carbohydrates and/or at least 18 En % lipids; wherein said composition having a caloric value of at least 100 kcal per daily dosage form, and wherein the whey proteins is acidic whey proteins.

25. A composition for stimulating appetite in a human comprising in a daily dosage form pantothenic acid or an equivalent of pantothenic acid selected from the group consisting of a salt, an ester or an ether of pantothenic acid, pantothenol, (R)-pantoate or a salt or an ester thereof, pantetheine or an ester or an ether thereof and coenzyme A, wherein the daily dosage form of pantothenic acid is 14 to 1000 mg of pantothenic acid, and wherein the daily dosage form of the equivalent of pantothenic acid is an equimolar amount of 14 to 1000 mg of pantothenic acid; and further comprising at least 15 En % proteins that comprise 1.8 to 6 g of methionine per 100 g of the proteins, 5.8 to 12.0 g of lysine per 100 g of the proteins, 1.5 to 4.0 g of tryptophan per 100 g of the proteins and at least 8 g of leucine per 100 g of the proteins, and optionally at least 32 En % carbohydrates and/or at least 18 En % lipids; wherein said composition having a caloric value of at least 100 kcal per daily dosage form, further comprising per daily dose 0.1 to 5 g beta-alanine when the composition comprises the pantothenic acid equivalent (R)-pantoate.

* * * * *

UNITED STATES PATENT AND TRADEMARK OFFICE
CERTIFICATE OF CORRECTION

PATENT NO.       : 8,388,949 B2                                          Page 1 of 1
APPLICATION NO.  : 10/584510
DATED            : March 5, 2013
INVENTOR(S)      : Robert Johan Joseph Hageman It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1519 days.

Signed and Sealed this
First Day of September, 2015

Michelle K. Lee
*Director of the United States Patent and Trademark Office*